(12) United States Patent
Herrin et al.

(10) Patent No.: US 6,309,487 B1
(45) Date of Patent: Oct. 30, 2001

(54) DISPOSABLE GARMENTS AND METHOD AND APPARATUS FOR MAKING

(76) Inventors: Robert M. Herrin, 5935 Groveline Dr., Orlando, FL (US) 32810; John M. Tharpe, 2606 Northgate, Albany, GA (US) 31707

( * ) Notice: Subject to any disclaimer, the term of this patent is extended or adjusted under 35 U.S.C. 154(b) by 62 days.

(21) Appl. No.: 08/628,190

(22) Filed: Apr. 5, 1996

Related U.S. Application Data (63) Continuation of application No. 08/384,429, filed on Feb. 6, 1995, which is a continuation of application No. 07/884,804, filed on May 19, 1992, now abandoned, which is a continuation-in-part of application No. 07/442,215, filed on Nov. 28, 1989, now Pat. No. 5,308,345.

(51) Int. Cl.[7] .............................. B32B 31/00; B29C 65/08
(52) U.S. Cl. .................... 156/73.1; 156/290; 156/308.4; 156/553; 156/580.1
(58) Field of Search ................... 156/73.1, 73.4, 156/290, 308.4, 324, 553, 580.1, 580.2; 264/442, 443, 444; 425/174.2

(56) References Cited

U.S. PATENT DOCUMENTS

| | | | |
|---|---|---|---|
| 2,034,716 | 3/1936 | Drefus | 26/97 |
| 2,283,137 | 5/1942 | Fine | 154/29 |
| 2,682,294 | 6/1954 | Langer | 154/42 |
| 2,702,406 | 2/1955 | Reed | 156/494 |
| 3,081,772 | 3/1963 | Brooks et al. | 112/252 |
| 3,161,563 | 12/1964 | Walker et al. | 26/97 |
| 3,417,751 | 12/1968 | Murdoch | 128/287 |
| 3,461,872 | 8/1969 | McConnell et al. | 128/287 |
| 3,738,081 * | 6/1973 | Heinzer | 53/180 |
| 3,765,973 | 10/1973 | Kramer | 156/73 |
| 3,828,784 | 8/1974 | Soephel | 604/385.1 |
| 3,850,780 * | 11/1974 | Crawford et al. | 156/583.1 |
| 4,151,031 | 4/1979 | Good et al. | 156/463 |
| 4,205,679 | 6/1980 | Repke et al. | 128/287 |
| 4,341,057 * | 7/1982 | Limousin | 53/553 |
| 4,433,527 * | 2/1984 | Ramsey et al. | 53/548 |
| 4,488,927 | 12/1984 | Hooper | 156/204 |
| 4,517,790 * | 5/1985 | Kreager | 53/552 |
| 4,610,681 | 9/1986 | Strohbeen et al. | 604/396 |
| 4,650,530 | 3/1987 | Mahoney et al. | 156/204 |
| 4,677,695 | 7/1987 | Van Gompel et al. | 2/237 |

(List continued on next page.)

FOREIGN PATENT DOCUMENTS

| | | | |
|---|---|---|---|
| 3715146 * | 12/1988 | (DE) | 156/380.2 |
| 0 234 658 | 2/1987 | (EP) . | |
| 0 405 575 A1 | 4/1992 | (EP) . | |
| 0 510 715 A1 | 4/1992 | (EP) . | |
| 0 631 766 A1 | 6/1993 | (EP) . | |
| 2 235 125 A | 2/1991 | (GB) . | |
| 2 257 652 A | 1/1993 | (GB) . | |
| 1-298203 | 2/1989 | (JP) . | |
| 3-231660 | 10/1991 | (JP) | 604/385.2 |
| 4-028363 | 1/1992 | (JP) | 604/385.2 |

*Primary Examiner*—James Sells
(74) *Attorney, Agent, or Firm*—Allen, Dyer, Doppelt, Milbrath & Gilchrist, P.A.

(57) ABSTRACT

Disposable garments of the training pants variety include a cuff which is rolled inwardly from the plane of each leg opening. The rolled cuff feature is obtained during production by stretching a unitary elastic sheet across the machine web in a direction lateral to the direction of manufacture, and then cutting leg openings through the elastic sheet and an adjacent outer web. The machinery for manufacturing the garments includes various features which facilitate the manufacture of this garment, including a reciprocating cutting knife and an associated accumulating conveyor for providing a reciprocal motion into the reciprocal knife. The manufacturing apparatus also includes features for maintaining core pads in the desired alignment, and various other features.

10 Claims, 9 Drawing Sheets

U.S. PATENT DOCUMENTS

| | | | |
|---|---|---|---|
| 4,743,241 | 5/1988 | Igaue et al. | 604/385 A |
| 4,747,846 | 5/1988 | Boland et al. | 604/385 A |
| 4,801,345 | 1/1989 | Dussaud et al. | 156/164 |
| 4,822,435 | 4/1989 | Igaue et al. | 156/164 |
| 4,834,740 | 5/1989 | Suzuki et al. | 604/385 A |
| 4,854,985 | 8/1989 | Soderlund et al. | 156/85 |
| 4,862,673 | 9/1989 | Francioni | 53/373 |
| 4,863,542 | 9/1989 | Oshefsky | 156/495 |
| 4,892,528 | 1/1990 | Suzuka et al. | 604/385.2 |
| 4,904,251 | 2/1990 | Igaue et al. | 604/385.2 |
| 4,909,804 | 3/1990 | Douglas | 604/385.2 |
| 4,925,520 | 5/1990 | Beaudoin et al. | 156/494 |
| 4,943,340 | 7/1990 | Ujimoto et al. | 156/496 |
| 5,043,036 | 8/1991 | Swenson | 156/160 |
| 5,055,103 | 10/1991 | Nomura et al. | 604/385.2 |
| 5,064,489 | 11/1991 | Ujimoto et al. | 156/164 |
| 5,080,741 | 1/1992 | Nomura et al. | 156/204 |
| 5,147,487 | 9/1992 | Nomura et al. | 156/164 |
| 5,163,932 | 11/1992 | Nomura et al. | 604/385.2 |
| 5,196,000 | 3/1993 | Clear et al. | 604/385.2 |
| 5,308,345 | 5/1994 | Herrin | 604/385.2 |
| 5,421,924 | 6/1995 | Ziegelhoffer et al. | 156/73.1 |

* cited by examiner

DISPOSABLE GARMENTS AND METHOD AND APPARATUS FOR MAKING

RELATED APPLICATIONS AND PATENTS

This application is a continuation of pending application Ser. No. 08/384,429 filed on Feb. 6, 1995, which is a continuation of application Ser. No. 07/884,804 filed on May 19, 1992, now abandoned, which is a continuation-in-part of application Ser. No. 07/442,215, filed Nov. 28, 1989, now U.S. Pat. 5,308,345.

BACKGROUND OF THE INVENTION

The present invention relates to disposable garments and methods and apparatus for making such garments.

The prior art teaches a wide variety of disposable diaper configurations, in which the finished diaper is a flat panel having adhesive tabs or the like, permitting the joinder of one end of the panel to the other, to fit the diaper panel from the infant's back, under the crotch and to the front of the waist. Examples of such arrangements are shown in the following U.S. Pat. Nos. 3,081,772 to Brooks et al; 3,417,751 to Murdoch; 4,892,528 to Suzuki et al; and 5,064,489 to Ujimoto et al.

There have also been developed in the prior art a variation of finished disposable training pants for infants, in which the finished product has opposing side seams joining the front and back panels of the garment assembly. Examples of these arrangements are shown in the following U.S. Pat. Nos. 4,743,239 to Cole; 4,743,241 to Igaue et al; 4,646,362 to Heran et al; 4,938,757 to Van Gompel et al; and 5,055,103 to Nomura et al; and 5,064,421 to Tracy.

The aforementioned U.S. Pat. No. 4,743,241 to Igaue et al discloses an elastic sheet adhered across the panel adjacent to the opposing leg openings, which serves as a liquid barrier for body fluids leaking from the center absorbent pad. A similar arrangement is disclosed in U.S. Pat. No. 3,417,751 to Murdoch.

SUMMARY OF THE INVENTION

The present invention is directed to disposable garments, particularly of the training pants variety, which include a rolled cuff inwardly from the plane of each leg opening, at least about the lower portion of the leg opening. Further, the present invention is directed to methods and apparatus for achieving this rolled cuff feature in a low cost and facile manner. The present invention also has the objective of providing methods and apparatus for achieving improvements and efficiencies in the manufacture of disposable garments of all types, including both disposable diapers, training pants, and incontinent garments for those who are elderly or infirmed.

In one form, a disposable garment in accordance with the present invention includes a panel of a material at least a portion of which is liquid impervious, the panel defining leg openings. The garment is provided with elastic means extending continuously about the-peripheral edge of each leg opening with the elastic means including a sheet of an elastic material stretched along an inside surface of the panel and about a substantial portion of the periphery of the corresponding leg opening, the elastic sheet being under sufficient stretch to draw the periphery of the leg opening into a curved elastic cuff when the garment is fitted about an infant. In this arrangement, the elastic sheet extends continuously around and to the peripheral edge of the corresponding leg opening.

In another form, the elastic sheet extends about the lower portion of the leg opening, with plural elastic bands extending about the remaining periphery of the leg opening at the upper portion on either side of the leg opening. In this arrangement, the elastic bands preferably also extend across the area covered by the corresponding elastic sheet, then laterally across the crotch area of the panel and then across a portion of the area covered by another elastic sheet about the opposing leg opening, with a similar pair of elastic bands being also disposed around the other side of the two leg openings.

A third form of construction for the disposable garment employs a second layer of elastic sheet extending between the leg openings, and longitudinally stretched between the leg holes. The second stretched elastic layer avoids the necessity for providing the elastic bands of the type described above, while at the same time providing a uniform gathering of material in the crotch area of the garment.

Preferably, the elastic sheet material is under a stretch on the order of five ounces per lineal inch for each inch of cross-width when installed across the panel, and extends at least 0.5 inches from the peripheral edge laterally across that portion of the panel where the elastic sheet is deposited.

In the manufacture of the garments, a unitary elastic sheet is stretched across the machine web in a direction lateral to the direction of manufacture, the elastic sheet having dimensions so as to cover an area of the web where leg openings for two adjacent garments will later be formed. Leg openings are then cut through each elastic sheet in the outer web, each leg opening lying within the boundaries of the corresponding elastic sheet and defining the peripheral edges of two leg openings, one each for the adjacent garments. The web is then later folded in half, so that the elastic sheet extends continuously around the leg opening. In this form of manufacture, the direction of stretch of the elastic sheet for each leg opening thus is generally parallel to the edge of the opening along the lower portion, the direction of stretch extending somewhat laterally away from the peripheral edge along that portion closest to the waist opening of the garment. Appropriate seams are formed along the sides between the front and back of the garment from the waist opening to the upper portion of each leg opening.

The present invention also is directed to -,manufacturing methods and apparatus, which includes a sequential series of operations formed at individual stations, or "sections", where the method and apparatus coact with the materials which make up the disposable garments.

One of the features of the present invention with respect to methods and apparatus for manufacturing such garments is the inclusion of a reciprocating "guillotine" cutting knife for severing the continuous web of absorbent material into individual pads. The use of a reciprocating knife reduces the hardness and sharpness of the edge of the pad, with respect to conventional rotary cutters. In order to accommodate the use of the reciprocating cutting blade, the present invention utilizes a conveying system in which the web of materials forming the pads are passed into an accumulator section which permits an elevated continuous feed from overhead onto a vacuum conveyor; the vacuum conveyor is then operated intermittently as required by the operation of the reciprocating cutting knife. The accumulator utilizes a retaining flap to keep the degree of accumulating "bend" in the continuous pad material to an acceptable level. The material forming the pad web is maintained against the vacuum conveyor with a curved bar extending in the direction of manufacture; the vacuum conveyor itself utilizes a woven material as the conveyor surface, with a fixed vacuum plate for drawing the pad web down against the woven conveyor surface. The reciprocating action of the knife across the laterally extending pad web is operated by an eccentric drive mechanism, and the cutting aperture below the reciprocating knife blade is angled in a V-shape, in order to facilitate a smooth cut.

A second feature of the present invention is located downstream of the reciprocal cutter. After cutting of the individual pads, the pads are then conveyed to a combining station and adhered to an outer carrier layer, or web. In order to insure that the pads are delivered exactly in a straight format to the combining station, the pad conveyor between the cutter and the combining section is provided with means for straightening any misaligned pads moving across the conveyor; this objective is achieved in a conveyor which also further achieves the objective of reaching near the throat of the reciprocal cutting knife, in order to receive each cut pad. This is achieved using multiple thin, plastic webbing strips for the conveyor surface, and a chain and dog drive positioned underneath the webbing conveyor, the chain having an eccentric drive to move each dog first slowly, then faster, then slowly again. The chain drives extend parallel'with the thin webbing, with the dogs extending through the webbing and into engagement with each pad. In operation, each straightening dog rises slowly between two of the conveyor webbing strips, then speeds up to engage the backside of a corresponding pad on opposite sides of the webbing, thereby straightening any misaligned pad. As the pad then nears the discharge end of the webbing conveyor, the eccentric drive of the chain assembly slows down each dog relative to the speed of the webbing conveyor, thereby causing each dog to effectively back away from the respective pad; each dog then is rotated below the level of the webbing conveyor.

Yet another feature of the method and apparatus relates to techniques for folding of an outer non-woven layer over the inner layers. In a preferred arrangement, the web making up the disposable garment includes an outer non-woven layer having a polyvinyl liquid impervious liner adhered to the outer non-woven layer, with the absorbent pad adhered to the liner, and with an inner non-woven layer adhered across the pad and the liquid impervious liner. The elastic sheet is disposed and adhered to across the inner surface of the outer non-woven layer, before disposition of the liquid impervious liner across the outer non-woven layer. Waistband elastic may also be adhered along the edges of the outer non-woven layer before fixing the polyvinyl barrier liner. Preferably, the outer non-woven layer has a lateral dimension relative to the direction of manufacture which is somewhat greater than the other layers, so that an edge portion of the outer layer extends beyond the other layers. This outer edge portion is then folded inwardly across the waistband elastic and the edges of the polyvinyl liner and then inner non-woven layer. This folded edge provides further comfort for the person wearing the garment, and also protects the waistband edge. This folding is achieved in a facile manner according to the present invention utilizing a feed roller having beveled ends, the dimensions for which correspond generally to the outwardly extending edge portion of the outer non-woven layer. These beveled ends permit the relaxation of the outer edge portion as the machine web passes underneath the roller under tension; thereafter, edge folding fixtures extend underneath and complete the folding of the edge portions with an adhesive. Of course, this edge folding function is achieved downstream from the combining section, where the absorbent pad is joined with the outer non-woven layer and the polyvinyl liner, and after the inner non-woven layer is affixed across the liner.

Following the edge folding operation, the machine web is passed into a leg hole cutting section', where leg holes are cut through the inner and outer non-woven layers, the polyvinyl liner and centrally through the elastic sheets. The dimensions of the elastic sheet are such as to extend outside of the leg hole dimensioned on the order of at least 0.5 inches, or more, as discussed above. Further, it will be appreciated that each leg hole defines a corresponding leg opening for adjacent garments which are eventually severed from the machine web. It is preferred that the leg hole cutting operation take place with a vacuum underneath the cutter, in order to draw away the waste product of that cutting operation.

Following the cutting of the leg holes, the machine web is then folded in half and passed into a seam weld section, where two adjacent seams are formed using an ultrasonic welder. In one arrangement, the anvil of the ultrasonic welder is heated to a temperature somewhat below the melting temperature of the polyvinyl liner, and the teeth on the anvil are sharpened to obtain penetration through all of the layers. The combination of the sharpened anvil teeth and the elevated temperature provide a highly reliable seam weld.

A second form of the ultrasonic seam welder utilizes an inflatable bladder behind the anvil, with the ultrasonic horn driven by an eccentric cam. These features permit a greater dwell time during the seaming operation.

The products are then passed into a unit cutter section, where the machine web is severed into individual garments.

These and other features of the present invention will be understood by those skilled in the art from the following accompanying drawings and description.

THE DRAWINGS

In FIGS. 7–16, three digit reference numerals are used to identify specific features of a corresponding portion of the system shown in FIGS. 1A and 1B, and in which the reference numeral for the section in FIGS. 1A and 1B has the same first two digit reference numeral (for example, in FIG. 7, three digit reference numerals 181, 182 and so forth refer to specific features of the accumulator section 18 in FIG. 1A).

DETAILED DESCRIPTION

The apparatus and method for making disposable garments will now be described with reference to FIG. 1A and 1B, with concurrent reference to FIGS. 2A and 2B. Thereafter, three forms of disposable garments made according to the method and using the apparatus is described with reference to FIGS. 3–6A and B, followed by a description of specific features of the apparatus as shown in FIGS. 7–16, and an alternate seam weld construction in FIGS. 17A–C.
The Method and Apparatus Noting FIGS. 1A and 2A, the apparatus 10 includes a fold section 12 using conventional techniques to fold an absorbent core material 16 and an outer tissue 14, in order to form a web of absorbent pad material 15. The output of the fold section is passed into an accumulator section 18, which is shown schematically in FIG. 1A to be elevated with respect to the fold section 12, and the downstream pad cutter section 20. As illustrated in FIG. 2A, the absorbent pad web 15 is cut into individual pads 22, each having a forward edge 24 and a rear edge 26, by cutting along a direction lateral to the direction of manufacture, as illustrated by arrows 30. The individually cut pads 22 are passed into a pad conveyor section 28, and then to a combining section 32.

In the combining section 32, an outer non-woven layer 34 is extended along the direction of manufacture shown by arrows 30, and provided with an appropriate adhesive, generally over the entire exposed surface of the non-woven layer 34. Waistband elastic strips 46 are extended along the adhesive-coated non-woven outer layer 34, again in the direction of manufacture shown by arrows 30, in order to provide a waistband elastic in a conventional manner. A liquid impervious liner 48 (for example, polyvinyl) is extended across the adhesive-coated non-woven layer 34, and then individual pads 22 are affixed to the exposed surface of the liner, using appropriate adhesives. The liner 48 either alone or in combination with the outer non-woven layer 34 serves as a carrier layer during the manufacturing operation.

In accordance with the present invention, there is provided a source of elastic sheet material 40, for example polyurethane foam or polyethylene sheeting, which is extended into a stretcher and applicator section 38, which is described in greater detail below with reference to FIGS. 12 and 13. As shown in FIG. 2A, the stretcher and applicator 38 cuts the elastic sheet into individual sheet segments 40, while simultaneously stretching each sheet segment 40 in a direction lateral to the direction of manufacture 30, as is; depicted by arrows 42 in FIG. 2A, and generally under the stretch conditions discussed above; that is, a stretch on the order of five ounces per lineal inch for each inch of cross-width (i.e., twenty-five ounces for a five inch length of one inch wide elastic). The individual elastic sheet segments 40 may be affixed to either the liquid impervious liner 48, or to the outer non-woven layer 34, as shown in FIG. 2A. The polyvinyl liner 48 and the individual pads 22 are respectively affixed to the outer non-woven layer 34 and the liner 48 with a conventional adhesive 36.

The output of the combining section is fed into another section where an inner non-woven layer 50 is fixed to the assembly by an adhesive across the liner 48. As is shown in FIG. 2A, the inner non-woven layer 50 and the liner 48 have a lateral dimension somewhat less than the corresponding dimension of the outer non-woven layer 34, so that the outer non-woven layer has peripheral edges 33, 35 extending beyond the periphery of the other two layers. After deposition of the inner non-woven layer at section 44, the assembly is then fed into an edge folding section 52. As schematically depicted in FIG. 2A, the peripheral edges 33, 35 of the outer non-woven layer 34 are then folded across the periphery of the inner non-woven layer 50 and joined thereto with an adhesive, as described in greater detail below with reference to FIGS. 14 and 15.

The output from the edge folding section 52 is then fed into a leg hole cutting section 54, which is operated inder a slight vacuum at 55, so as to remove the scrap without interfering with tie manufacture of the assembly. Noting FIG. 2A, each leg hole 56 is cut centrally in the web defined by the layers 34, 48 and 50 between adjacent pads 22, and centrally within the peripheral boundary of a corresponding elastic sheet 40; preferably, the dimensions of the leg hole and the elastic sheet are selected so that a minimum of 0.5 inches of the elastic sheet, and suitably an even greater dimension, extend from the peripheral edge of the leg hole 56 to the boundary of the elastic sheet 40. It will of course be appreciated that the cutting of the leg hole 56 centrally in the elastic sheet 40 insures that the elastic sheet extends to the very edge of the leg hole. As will be discussed in greater detail below with reference to FIGS. 3–5, this particular feature enables the disposable garment to achieve a desirable inwardly rolled cuff which assists in defining a liquid barrier.

Figure 2A:
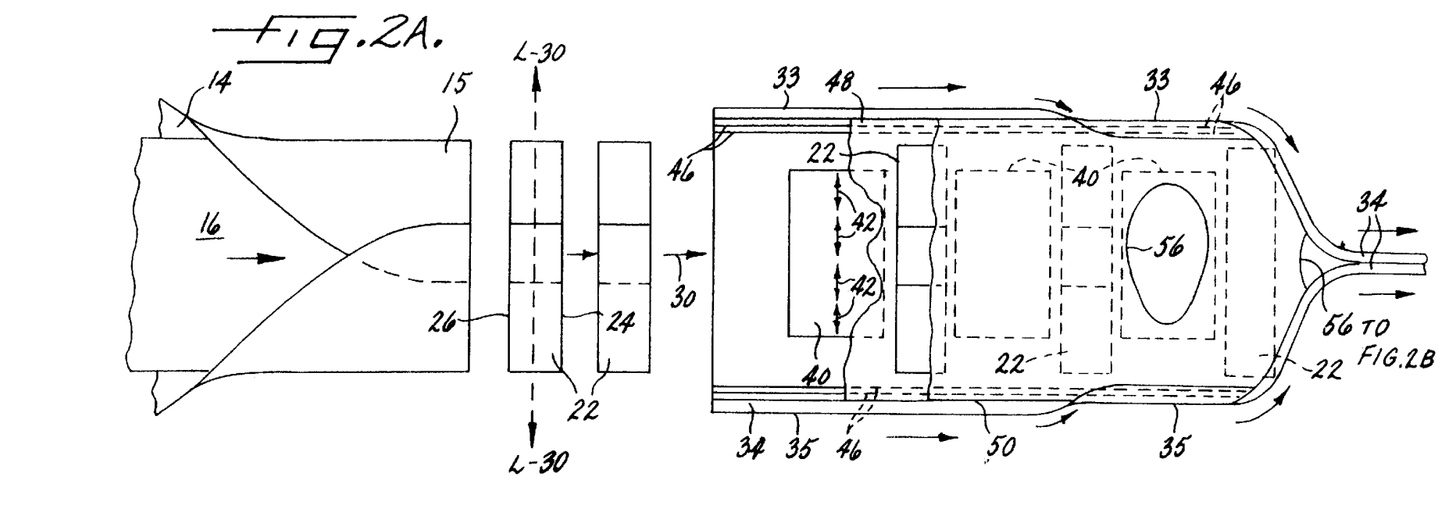
FIGS. 2A and 2B are top and side views, respectively, illustrating the component portions and manner of fabrication of disposable garments in accordance with the present invention and in which various locations along the direction of operation in FIGS. 2A and 2B generally correspond to the location of the various sections of the system illustrated in FIGS. 1A and 1B, and in which the direction of manufacture is from left to right in both Figures.
Figure 2B:
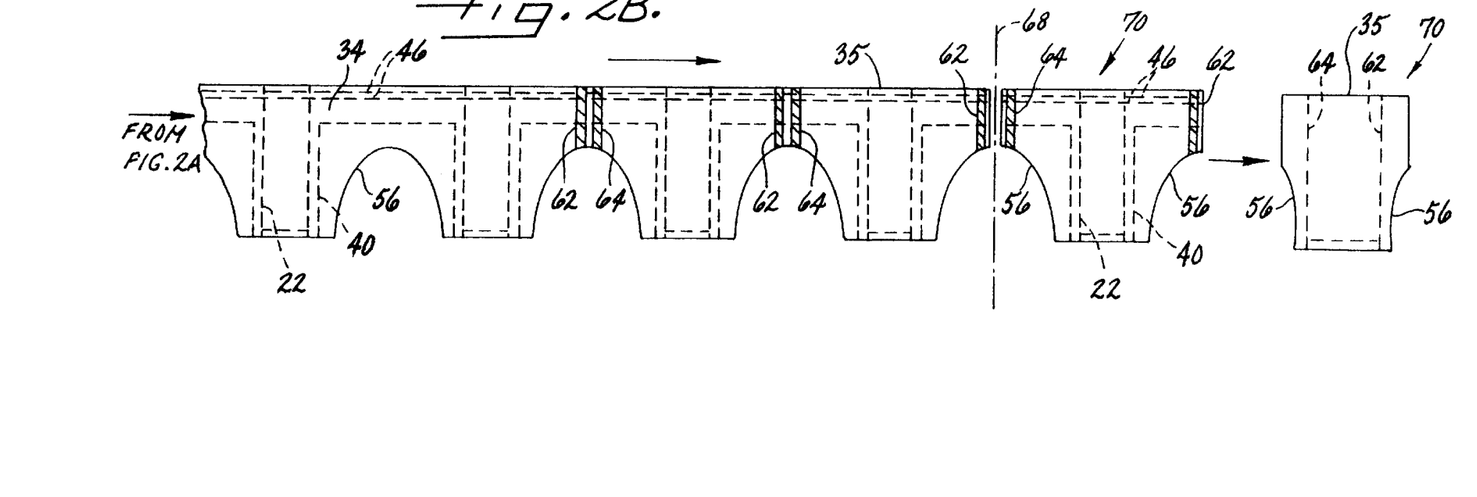

After passing out of the leg hole cutting section 54, the assembly is fed into a web folding section 58, where the entire web is folded upon itself, as depicted along the left hand side of FIG. 2B. The web is then fed into a seam welding section 60, where parallel seams are formed between the upper edge of the web and the upper extremity of each leg hole 56; preferably, this is achieved utilizing an ultrasonic welder and a rotating anvil which is heated to a temperature slightly below the melting point of the polyvinyl liner 48, and below the ignition temperature of the non-woven layers 34 and 50.

The output from the seam welding section is then passed into a unit cutter section 66, where the web is cut into individual garments 70. Each garment is then conveyed into a blower section 67, where air is blown into the individual garment, following which each individual garment is subjected to a vacuum at 69 to draw the intermediate seam welds inwardly to form a compact unit for packaging purposes.

Figure 3:
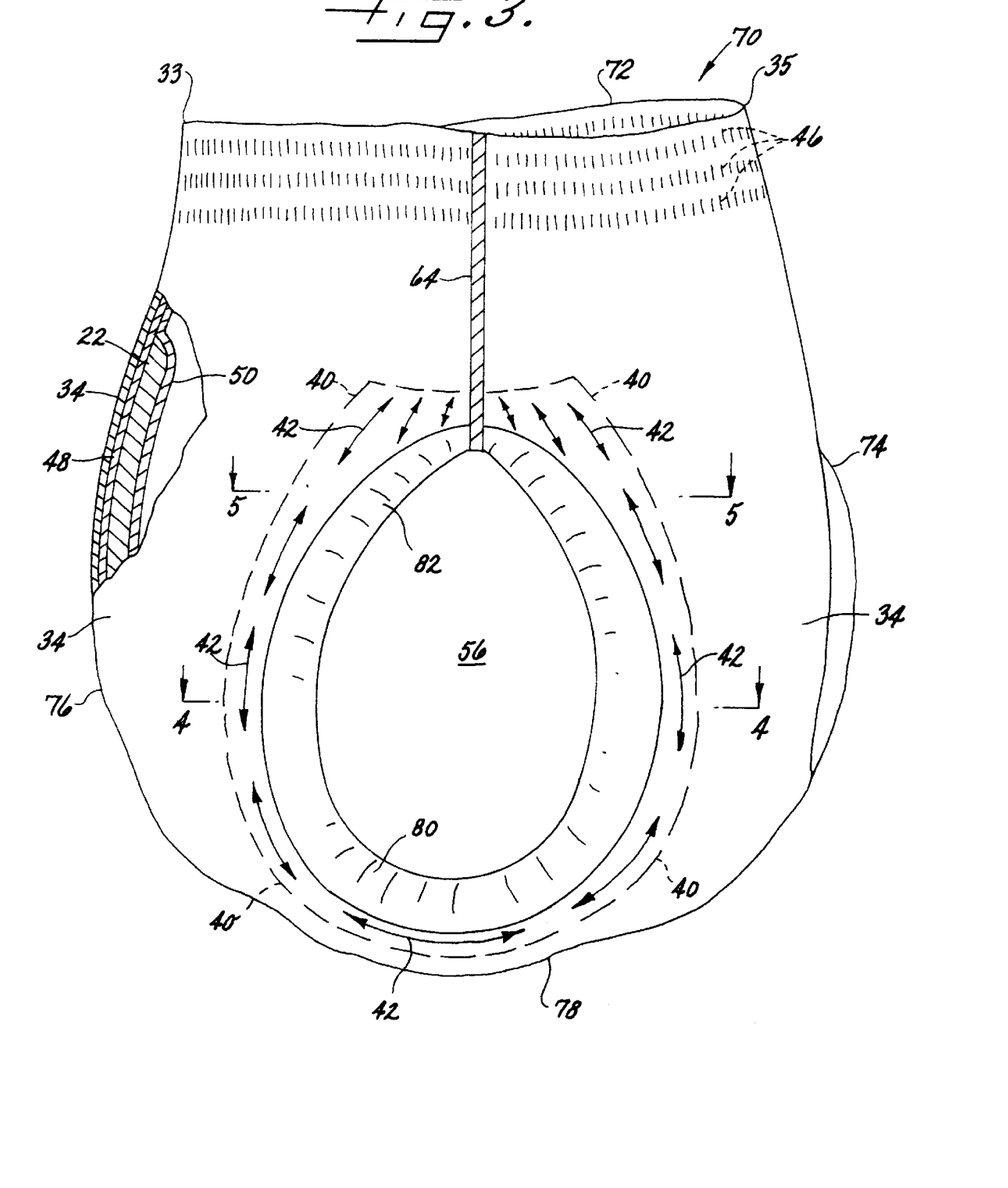
FIG. 3 is a side elevation, partially in cross section, of a disposable garment in accordance with the present invention.
Figure 4:
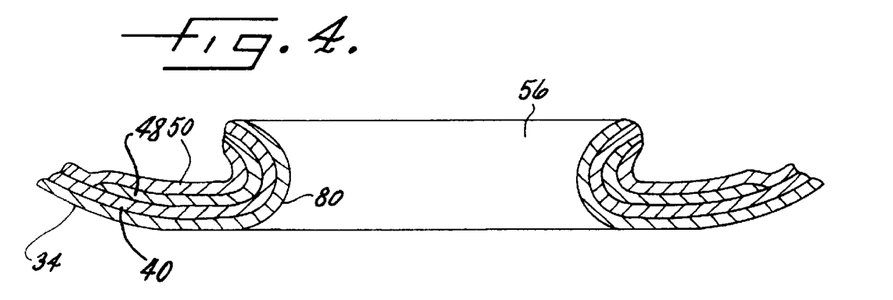
FIG. 4 is a cross section of a portion of the disposable garment shown in FIG. 3, taken along the line 4—4.
Figure 5:
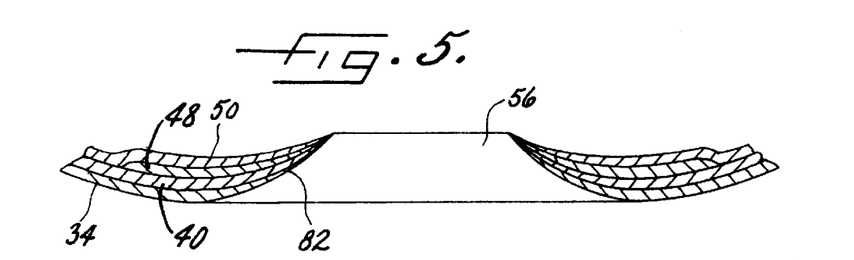
FIG. 5 is another cross section of a portion of the disposable garment shown in FIG. 3, taken along the line 5—5.

A First Embodiment of the Disposable Garment (FIGS. 3–5)

Construction details of a first form of the disposable garment 70 are depicted in FIGS. 3–5. As constructed, the garment 70 includes a waistband opening 72, a front panel 74, an opposing rear panel 76 and a crotch area 78; it will of course be understood that the front and back panels and the crotch area 74, 76 and 78 are formed from the assembly of materials in accordance with the method depicted in FIGS. 2A and 2B, and includes (as shown in the cut away portion in FIG. 3) the outer non-woven layer 34, the liner 48, absorbent pad 22 and inner non-woven layer 50, with the elastic waistbands 46 and seam 64.

The portion of the elastic sheet 40 remaining with the individual garment 70 after formation of the leg opening 56, folding of the web and welding of the seam 64 is depicted by a dotted line in FIG. 3. Arrows 42 also depict the direction of stretch of the elastic sheet 40. As discussed above, the cutting of the leg opening 56 through the field of the elastic sheet 40 is accomplished so as to extend to the extreme periphery of the opening 56. This, together with the folding of the web to form the front and back panels 74, 76 relieves the stretching of the elastic sheet 40 along the periphery of the leg opening 56, and causes the elastic sheet along the periphery to roll into an inwardly-directed cuff along the periphery of the leg opening 56. However, because of the variance of the stretch represented by arrows 42 from the lower portion 80 of the leg opening 56 to the upper portion 82, the degree of roll of the cuff varies from the lower portion to the upper portion. This is shown by comparison of FIGS. 4 and 5, where the lower portion 80 of the rolled cuff is shown to be greater than the upper portion 82 of FIG. 5. This variance of the rolled cuff from the lower portion is desirable, since the upper portion does not require as great a roll in the cuff for purposes of providing a liquid barrier, and also provides greater comfort to the person wearing the garment 70.

Figure 6A:
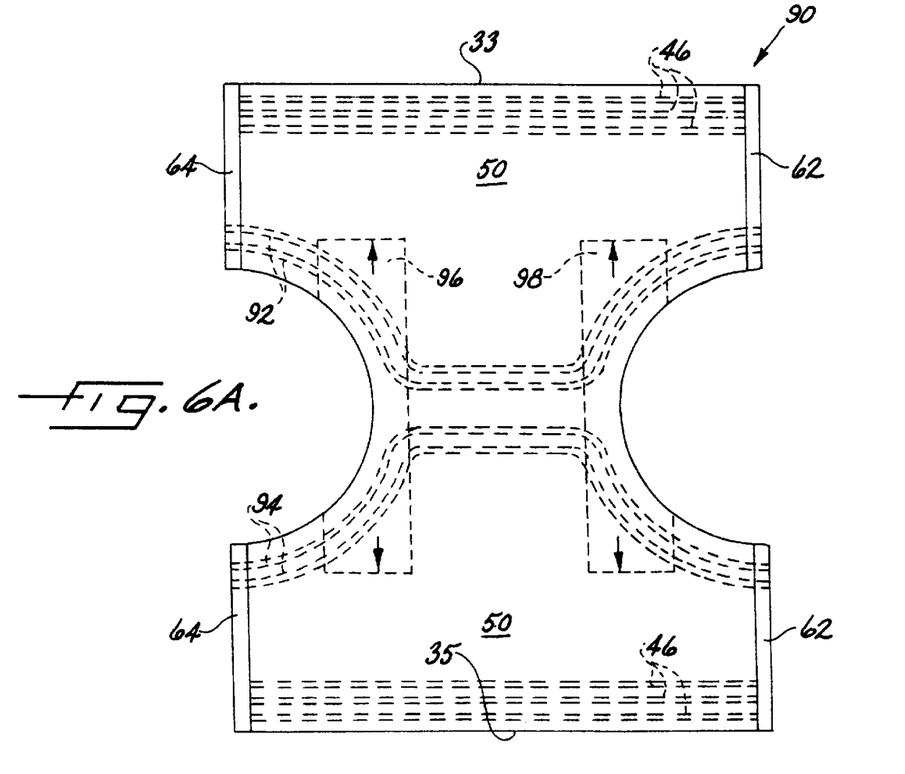
FIG. 6A is a top view of a second form of a disposable garment in accordance with the present invention.
Figure 6B:
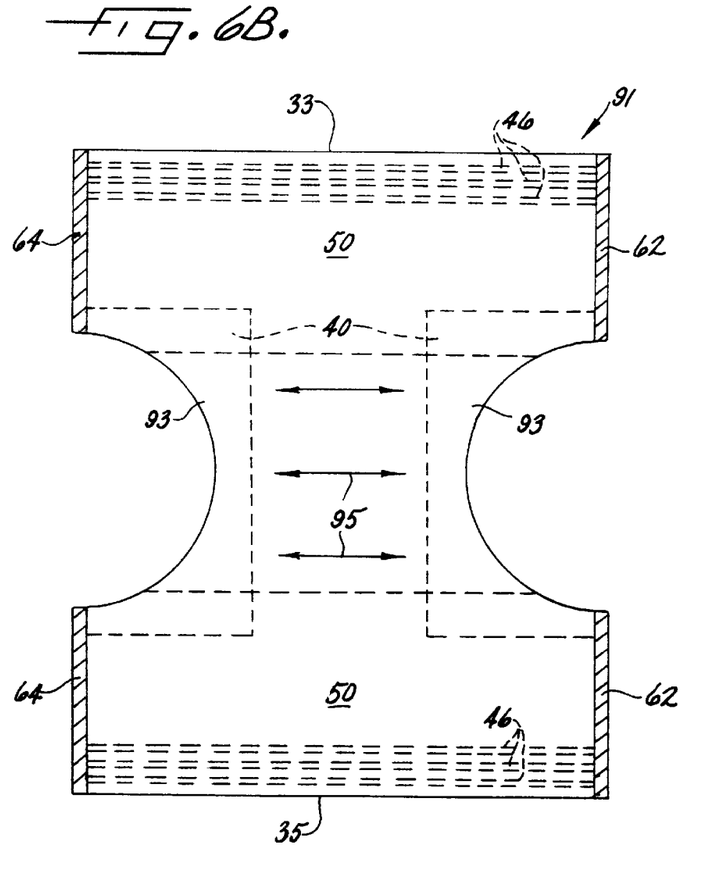
FIG. 6B is a top view of a third form of a disposable garment according to this invention.

Other Forms of the Disposable Garment Construction (FIGS. 6A and B)

A second alternate form of construction of the disposable garment in accordance with the present invention is shown in FIG. 6A and referred to generally by the reference numeral 90.

Disposable garment 90 includes various features of the garment 70 shown in FIGS. 3–5, which are referred to by the same reference numerals, including waistband elastic 46, seams 62, 64, inner non-woven layer 50, pad 22 and leg openings 56. The construction of disposable garment 90 from the construction of garment 70 in FIG. 3 through the use of elastic bands 92 and 94 which extend continuously around the periphery of opposite sides of each leg opening and across a portion of the same area covered by elastic sheets 96, 98 and also across the crotch area of the garment 90 to the opposite leg opening 56. Further, the elastic sheets 96, 98 may be drawn back slightly from the respective seams 64, 62 so as to extend essentially about the peripheral edge of the lower portion of the leg opening 56 after being folded.

A third form of construction of a disposable garment in accordance with the present invention is shown in FIG. 6B and referred to there by the reference numeral 91.

The disposable garment 91 also includes the various features of the garments 70 and 90 shown in FIGS. 3–5 and 6A, to the extent that those various features are referred to by the same reference numerals. Additionally, the garment 91 includes a second layer of elastic sheeting extending between the leg openings, and longitudinally stretched in the direction of the arrows 95 in FIG. 6B. The stretched elastic layer 93 avoids the necessity for providing the elastic bands 92 and 94 of FIG. 6A, while at tne same time providing a uniform gathering of material in the crotch area of the garment 91.

Figure 7:
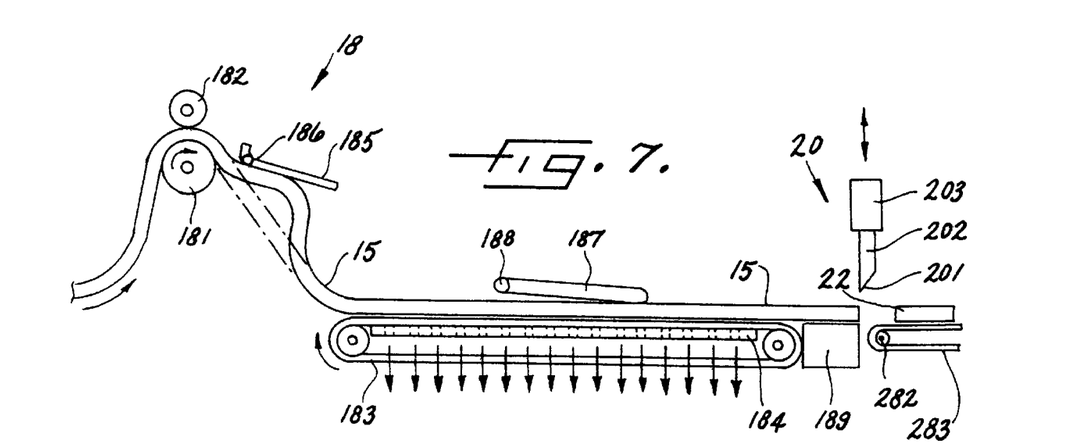
FIG. 7 is a side elevation illustrating the accumulator section of the system shown in FIG. 1A, and in which the direction of manufacture is from left to right in the Figure.

The Accumulator Section (FIG. 7)

Figure 1A:
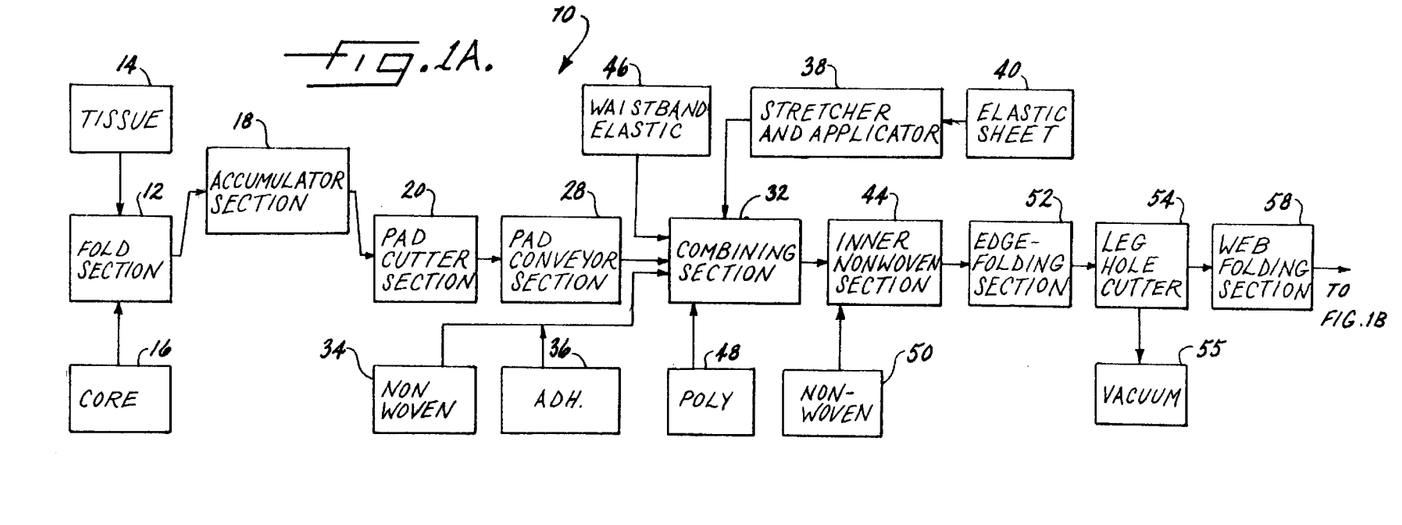
FIGS. 1A and 1B are flow charts illustrating the system, method and apparatus of the present invention, as used in the manufacture of disposal garments, and in which the direction of manufacture is from left to right in both Figures.
Figure 1B:
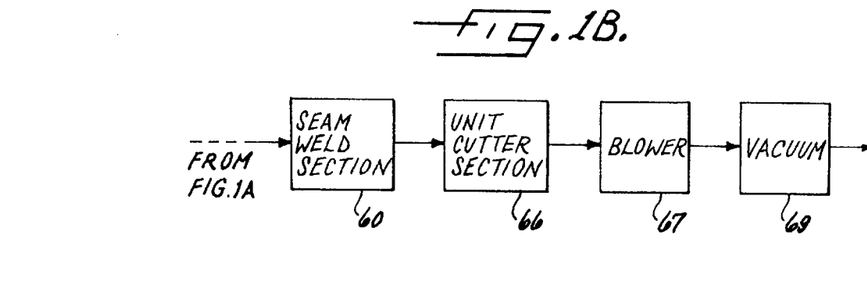

Details of the accumulator section 18 of FIG. 1A are shown in FIG. 7.

As shown on the left hand side of FIG. 7, the absorbent pad web 15 is extended across elevated rollers 181, 182 which operate continuously to receive the feed of the web 15. The rollers 181, 182 then feed the web 15 downwardly across an indexing conveyor 183, which preferably consists of a wire mesh extending across a fixed vacuum plate 184 having holes therein permitting a vacuum to be drawn, as shown by arrows. the accumulator section 18 further includes a control plate 185 pivoted at 186, and extending across the web 15 somewhat below the continuous feed rollers 181, 182. Similarly, there is a pressure rod 187 pivoted at 188 extending across the absorbent pad web 15 and over the indexing conveyor 183.

In operation, the absorbent pad web 15 is drawn into fixed engagement with the mesh surface of the indexing conveyor 183 via the vacuum plate 184. The indexing conveyor 183 is operated on a "stop-start", or intermittent basis, as required by the operation of the reciprocating cutting blade 20 described below in greater detail with reference to FIGS. 8 and 9, but the details of which are also depicted in FIG. 7. Thus, the rollers 181 and 182 are continuously feeding the web 15 onto a conveyor which only operates on an intermittent basis; therefore, the web 15 is subjected to a buckling, as shown below the control plate 185. The degree of buckle is controlled by the plate 185, to insure that the direction of the web continues along the surface of the intermittent indexing conveyor 183. The pressure rod 187 also insures that any buckling does not extend beyond the central area of the indexing conveyor 183.

As shown on the right hand side of FIG. 7, the indexing conveyor 183 forces the absorbent pad web 15 across a fixed mandrel 189 in the throat of the cutting section 20, described next.

Figure 8:
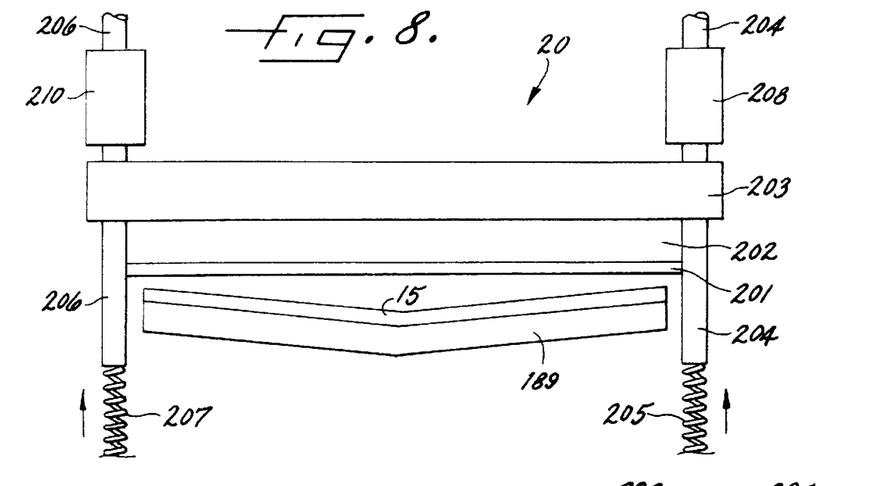
FIG. 8 is a front elevation and FIG. 9 is a side elevation, both illustrating features of the reciprocal knife cutting section of the system of FIG. 1A.
Figure 9:
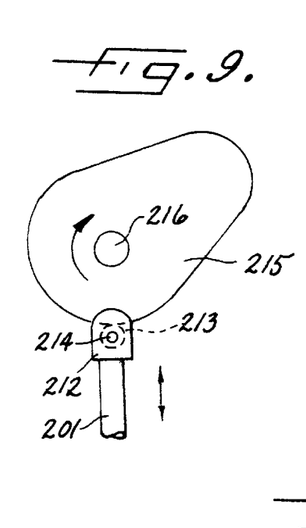

The Pad Cutting Section (FIGS. 8 and 9)

As discussed briefly above, the pad cutting section 20 utilizes a reciprocating "guillotine"-type of cutter, which achieves certain benefits with respect to the formation of the cut edge in the absorbent pads 22.

Referring to FIG. 8, the cutting section 20 includes a blade 202 terminating in a cutting edge 201, and carried by a cross plate 203 extending across the machine direction. The plate 203 is carried by reciprocating rods 204, 206 which are supported by springs 205, 207 for biasing in an upward direction. The reciprocating rods 204, 206 are supported by respective bearing blocks 208, 210. As shown in the front view of FIG. 8, the mandrel 189 has a V-configuration, such that the absorbent pad web 15 is sheared downwardly from each side to the central portion of the mandrel.

Noting FIG. 9, the reciprocating motion of the rods 204, 206 is controlled by an eccentric 215 rotating-about a shaft 216, and engaging a rotating element 213 mounted on a pivot axis 214 and which is supported by a yoke 212 at the upper extremity of each rod 204, 206. The use of an eccentric cam surface to control the operation of the cutting blade 201, together with the shape of the cutting throat defined by mandrel 189 insures a smooth, even and sharp cut through the absorbent pad web 15, to define individual pads 22.

Figure 10:
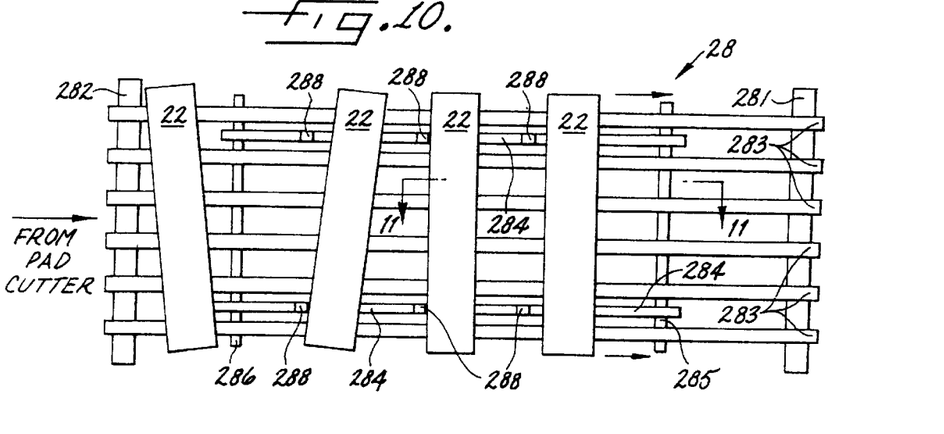
FIG. 10 is a top plan view of the pad conveyor section of the system shown in FIG. 1A.
Figure 11:
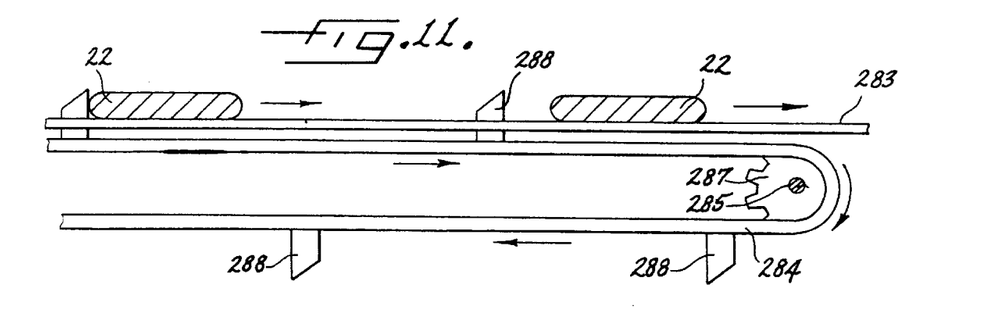
FIG. 11 is a cross section of a portion of the conveyor shown in FIG. 10, taken along the lines 11—11.

Pad Conveyor Section (FIGS. 10 and 11)

Details of the pad conveyor section 28 of FIG. 1A are shown in FIGS. 10 and 11. The pad conveyor includes a pair of rotating shafts 281, 282 which extend laterally across the direction of manufacture, and support plural vinyl conveyor straps 283 along the manufacturing direction. As is depicted in FIG. 7, the conveyor webs 283 are extended into close proximity to the throat of the pad cutter 20.

A pair of chain drives 284 are supported parallel to and underneath the webbing 283, each chain drive 284 spaced between two of the webbing strips. The chain drives are supported by shafts 285, 286 and an eccentric drive 287 (FIG. 11). Plural straightening dogs 288 are dimensioned vertically to extend upwardly from the respective chain drives 284 and above the level of the webbing strips 283. As is depicted in FIG. 10, the eccentric drive 287 imparts a "slow-fast-slow" pace to the movement of the straightening dogs, in order that the dogs may first extend upwardly between adjacent strips 283, then be speeded up to engage the backside of a corresponding pad 22 to straighten the position of any misaligned pad across the lateral direction, and then slow down and back away from the back edge of the corresponding pad, before rotating underneath the chain drive as shown in FIG. 11. Of course, the pad 22 is then discharged from the pad conveyor 28 on the right hand side of FIG. 10, and progresses to the combining section 32 (FIG. 1A).

Figure 12:
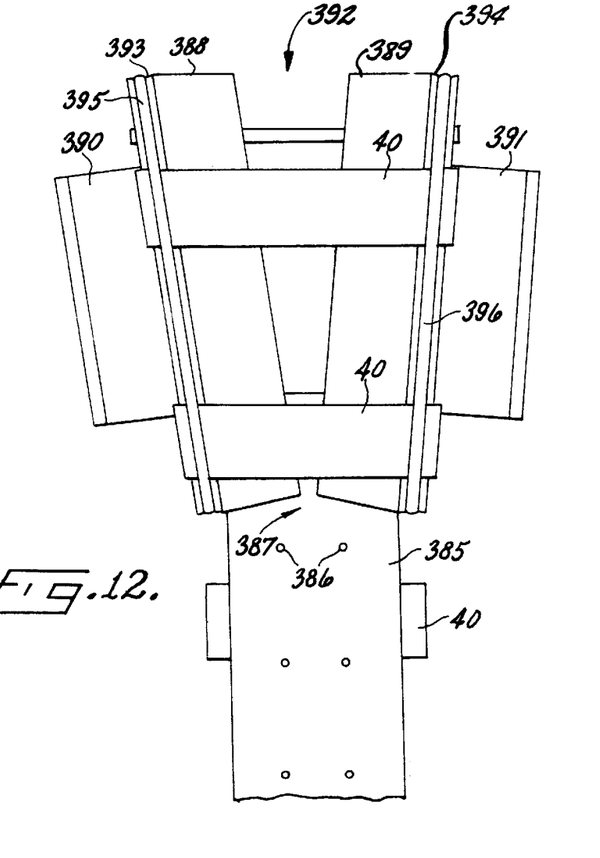
FIGS. 12 and 13 are top and side views, respectively, of the stretcher and applicator section of the system shown in FIG. 1A, and in which the direction of manufacture is from the bottom upwardly in FIG. 12 and right to left in FIG. 13.
Figure 13:
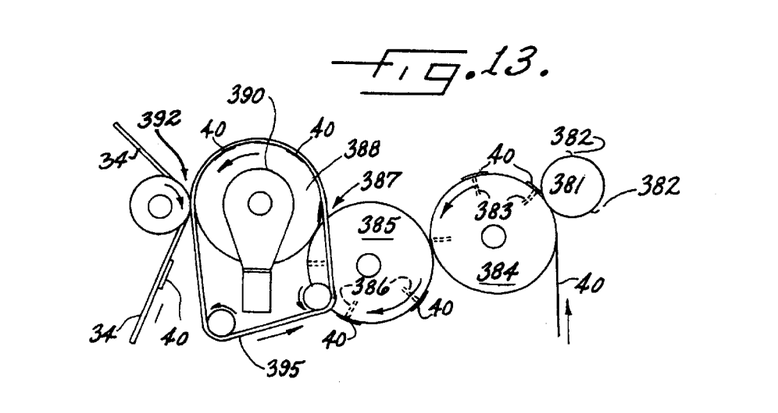

Stretcher and Applicator Section (FIGS. 12 and 13)

The stretcher and applicator section is described in application Ser. No. 07/442,215 U.S. Pat. No. 5,308,345 which is incorporated here by reference.

As shown in FIG. 13, a web of the elastic sheet 40 (i.e., urethane foam or polyethylene) is passed into a knife roller 381 having knife blades 382, at which point the web of elastic sheet is cut into individual sheet segments 40. the knife roller 381 cuts the elastic sheet lengths 40, and vacuum chucks 383 on anvil 384 carries the elastic sheet lengths 40 to a transfer roller 385.

Noting both FIGS. 12 and 13, at an appropriate transfer point, the individual elastic sheets 40 are received along the surface of the transfer roller 385 which also includes vacuum chucks 386. The vacuum chucks 386 hold the individual elastic lengths 40 across the transfer surface of the transfer roller 385, until such time as the individual sheets 40 are fed into an entry point 387 of stretching rollers 388, 389. As is particularly shown in FIG. 12, the crosswise dimension of the transfer surface of the transfer roller 385 is substantially less than the lengthwise dimension of each elastic sheet 40, and is approximately equal to or less than the spacing between gripping belts 395, 396 on the stretching rollers 388, 389 at the entry point 387.

The stretching rollers 388, 389 are mounted on respective hubs 390, 391, each of which may be individually adjusted at an outwardly skewed angle from the entry point 387 to an exit point 392. Each rotating stretching roller 388, 389 also includes a corresponding peripheral groove 393, 394 across which passes a corresponding smooth surface gripping belt 395, 396, each of which is dimensioned to fit within the corresponding peripheral groove 393, 394. As each gripping belt 395, 396 approaches the periphery of the corresponding roller 388, 389 at the entry point 387, an adjacent one of the elastic sheets 40 are picked up at the transfer point by the gripping belts and pinched into the corresponding groove 393, 394. As the skewed rollers 388, 389 are rotated, the gripping belts hold the sheets in place, and the skewed angle effectuates the desired degree of stretching. Thereafter, as is shown in FIG. 13, the individual sheets 40 are discharges at area 392 onto the web of the outer non-woven layer 34.

Figure 14:
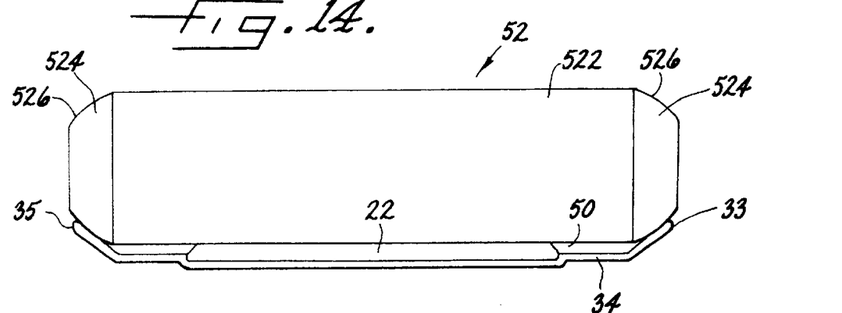
FIG. 14 is a front view of a portion of the edge-folding section in the system shown in FIG. 1A.
Figure 15:
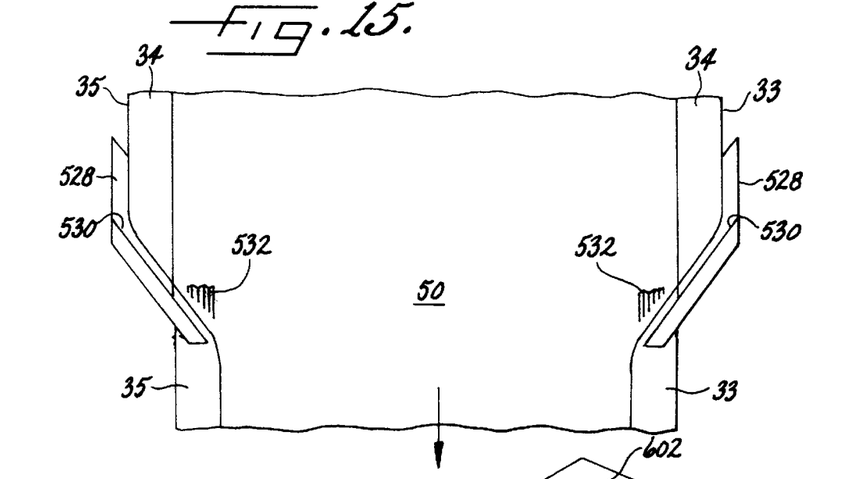
FIG. 15 is top view of that edge folding section with the direction of manufacture from the top downwardly.

Edge Folding Section (FIGS. 14 and 15)

The edge folding section 52 includes a pressure roller 522, under which the combined web assembly including the outer non-woven layer 34, liner (not depicted in FIG. 14), absorbent pad 22 and inner non-woven layer 50 are all passed. As is illustrated in FIG. 14, the pressure roller 522 includes inwardly tapered, low friction surfaces which are dimensioned to engage only the extended edge portions 33, 35 of the outer non-woven layer 34. Because the tension of the web is relieved by the taper 526 on the in caps 524, the edge portions 33, 35 are lifted upwardly. Thereafter, the web is passed across edge folders 528, each of which includes a tapered fold surface 530 for receiving the elevated edge portions 33, 35. A glue joint 532 is then directed across the outer edge of the inner non-woven layer 50, for receiving the folded edges 33, 35 of the outer non-woven layer 34.

Seam Weld Section (FIGS. 16) and 17A–C

Figure 16:
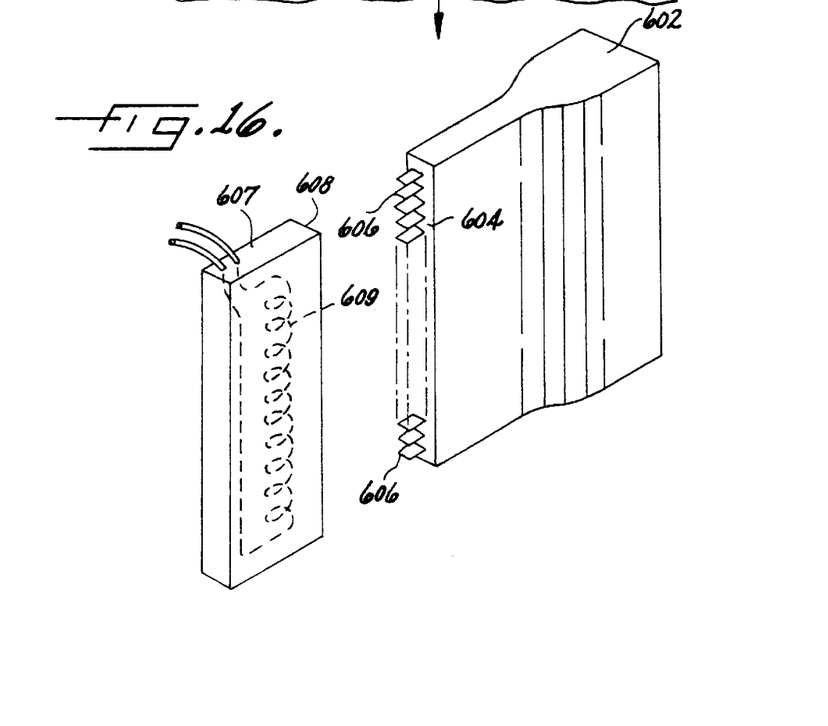
FIG. 16 is a perspective view illustrating one form of the seam welding section of the system in FIG. 1B.

As discussed above, the seam weld section 60 (FIG. 1B) utilizes an ultrasonic welder including weld head 602 having a face 604 with protruding weld pins 606. In accordance with the present invention, the pins 606 are sharpened to a sufficient degree to insure penetration through the entire web assembly, including the outer non-woven layer 34, elastic sheet 40, liner 48 and inner non-woven layer 50. Further in accordance with the present invention, the ultrasonic welder is operated in conjunction with a rotating anvil 607 having an anvil face 608 which is heated by an internal heating coil 609 to a temperature which is slightly below the melting temperature of the polyvinyl liner 48, and of course below the ignition temperature of the inner and outer non-woven layers 34, 50. It has been found that this particular arrangement shown in FIG. 16 provides desirable seam welds in a facile manner.

Figures 17A, 17B, 17C:
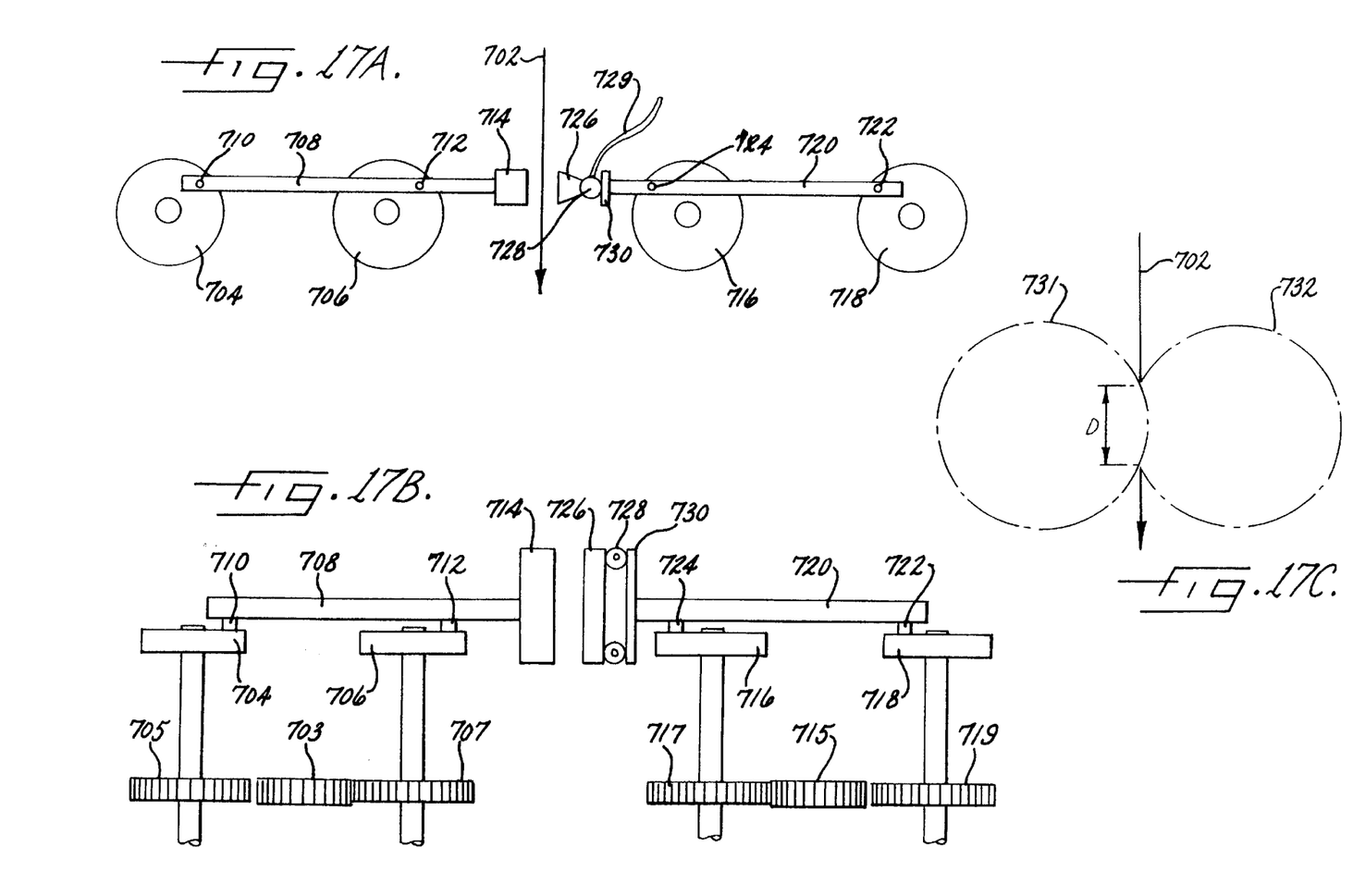
FIGS. 17A and 17B are top and side views illustrating construction details for a second form of the seam welding section, with the direction of manufacture downwardly in FIG. 17A and toward the viewer in FIG. 17B.
FIG. 17C is a diagram illustrating the movement of the horn and anvil in the construction of FIGS. 17A and 17B.

A second form of the seam welding section is depicted in FIGS. 17A–C. In this arrangement, the seam welding section includes opposing pairs of rotating drive wheels 704, 706 and 716, 718. Each pair of drive wheels is pivotally connected respectively at 710, 712 and 722, 724 to a corresponding drive rod 708, 720. (As shown in FIG. 17B, each of the drive wheels is in turn rotated by a corresponding shaft and gear arrangement, including corresponding gears 705, 707 and 717, 719, with each the drive gear being driven by a respective pinion 703, 715).

A conventional ultrasonic horn 714 is mounted on the forward extremity of the drive rod 708, and a conventional ultrasonic anvil 726 is mounted at the extremity of the second drive rod 720. In accordance with the present invention, the anvil is coupled to a back plate 730 via an air bladder 728 which is capable of being alternately inflated and deflated from an air supply 729. This construction permits the anvil 726 to be inflated outwardly toward the horn 714, and also imparts a significant degree of "give" to the anvil 726 via the air bladder 728.

In operation, rotation of each pair of drive wheels 704, 706 and 716, 718 results in the reciprocal movement of the corresponding drive rod 708, 720 toward the machine web, the web being represented by arrow 702 in FIGS. 17A and 17C. It will of course be appreciated by those skilled in the ultrasonic welding art that without the presence of the compressible bladder 728, there is only one tangential point where the ultrasonic horn 714 and the anvil 726 may come in contact with each other, in order to avoid any damage to either part. However, with the provision of the inflatable bladder 728, the anvil 726 is imparted with a significant degree of "give" or compressibility, thereby permitting the horn 714 and the anvil 726 to be in contact with each other for a much greater period of time during movement of the web (represented by arrow 702) along the direction of travel. This results in a much better forming of weld seams like seam 62 and 64 in FIG. 2B. This greater dimension of contact is represented by dimension D in FIG. 17C, in which circles 730 and 732 respectively depict the circular motions of the horn 714 and anvil 726 during movement of the drive rods 708, 720.

SUMMARY

There has been disclosed above a system and method for manufacturing disposable garments, the system including various apparatus features. Further, the disposable garments 70 and 90 of FIGS. 3–6 provide a cuff which extends inwardly from the plane of the leg hole, to provide a liquid barrier at least in the region of the lower portion of the leg opening. This is achieved utilizing an elastic sheet which may be stretched to a sufficient degree to insure achieving the desired rolled cuff feature, and in a manner which lends itself to high speed, low cost manufacturing techniques.

This concludes the description of the preferred embodiments. A reading by those skilled in the art will bring to mind various changes without departing from the spirit and scope of the invention. It is intended, however, that the invention only be limited by the following appended claims.

What is claimed is:

1. A method of sealing a multi-ply diaper web comprising the steps of:
    providing an elongated ultrasonic horn assembly above a linear path and an elongated anvil assembly below said path, each of said assemblies having an end adjacent said path,
    moving each assembly through a circular orbit while maintaining each elongated assembly in a vertical orientation and with said orbits intersecting at two spaced apart points in said path,
    continuously advancing a multi-ply web along said path, and
    resiliently contacting said assembly ends between said two spaced apart points to provide area contact between said assemblies and without relative movement between said webs and said assemblies.

2. A method of sealing a multi-ply diaper web comprising the steps of:
    providing an elongated ultrasonic horn assembly above a linear path and an elongated anvil assembly below said path, each of said assemblies having an end adjacent said path;
    orbiting each assembly while maintaining each elongated assembly in a vertical orientation and with said orbits intersecting at two spaced apart points in said path;
    continuously advancing a multi-ply web along said path; and
    resiliently contacting said assembly ends between said two spaced apart points to deform one of said orbits while clamping said web.

3. Apparatus for ultrasonic sealing of disposable diapers comprising a frame, conveyor means on said frame for advancing elongated diaper component webs along a linear path, a horn assembly including a horn orbitally mounted on said frame on one side of said path, an anvil assembly orbitally mounted on the other side of said path and aligned with said horn assembly so as to clamp said webs together for sealing the same, linkage means connecting each assembly to said frame so as to maintain each assembly in the same orientation throughout the orbit, one of said assemblies including resilient means to enable said one assembly to yield resiliently upon contact with the other of said assemblies while still clamping said webs and traveling therewith in said orientation during sealing.

4. The apparatus of claim 3 in which said anvil assembly includes a single anvil, each of said horn and anvil having an area of contact extending longitudinally of said path.

5. The apparatus of claim 3 in which said resilient means is arranged and constructed to provide a generally flat portion of the orbit of said one assembly, said flat portion being positioned adjacent said linear path.

6. The apparatus of claim 5 in which said resilient means includes airmount cylinder means.

7. Apparatus for ultrasonic sealing of disposable diapers comprising a frame, conveyor means on said frame for advancing elongated diaper component webs along a linear path, a horn assembly including a horn orbitally mounted on said frame on one side of said path, an anvil assembly orbitally mounted on the other side of said path and aligned with said horn assembly so as to clamp said webs together for sealing the same linkage means connecting each assembly to said frame so as to maintain each assembly in the same orientation throughout the orbit, one of said assemblies including resilient means to enable said one assembly to yield resiliently upon contact with the other of said assemblies, said linkage means including a four bar linkage arranged in a parallelogram for each assembly and including two plates extending perpendicular to said linear path and two arms pivotally connected at spaced apart points to each of said plates.

8. The apparatus of claim 7 in which said one of said resilient means is arranged and constructed to provide a generally flat portion of the orbit of said one assembly, said flat portion being positioned adjacent said linear path.

9. The apparatus of claim 7 in which said resilient means includes airmount cylinder means.

10. Apparatus for ultrasonic sea ling of disposable diapers comprising a frame, conveyor means on said frame for advancing elongated diaper component webs along a linear path, a horn assembly including a horn mounted on said frame for movement in a circular orbit on one side of said path, an anvil assembly mounted on said frame the other side of said path for movement in a circular orbit and aligned with said horn assembly so as to clamp said webs together for sealing the same, linkage means connecting each assembly to said frame so as to maintain each assembly in the same orientation throughout the orbit, one of said assemblies including resilient means to enable said one assembly to yield resiliently upon contact with the other of said assemblies to deform the circular orbit of said one assembly during clamping of said web and to provide area contact between said horn and anvil assemblies and without relative movement between said webs and said assemblies.

* * * * *

UNITED STATES PATENT AND TRADEMARK OFFICE
CERTIFICATE OF CORRECTION

PATENT NO.    : 6,309,487 B1
DATED         : October 30, 2001
INVENTOR(S)   : Herrin et al.

It is certified that error appears in the above-identified patent and that said Letters Patent is hereby corrected as shown below:

Column 1,
Line 30, please delete "and".
Line 58, please delete "the-peripheral" and insert -- the peripheral -- therefor.

Column 2,
Line 42, please delete "-,manufacturing" and insert -- manufacturing -- therefor.
Line 45, please delete "coact" and insert -- co-act -- therefor.

Column 3,
Line 24, please delete "parallel' " and insert -- parallel -- therefor.

Column 4,
Line 4, please delete "section' " and insert -- section -- therefor.
Line 39, please delete "dispoal" and insert -- dispoable -- therefor.

Column 6,
Line 36, please delete "inder" and insert -- under -- therefor.

Column 8,
Line 18, please delete "the" and insert -- The -- therefor.

Column 9,
Line 34, please delete "the" and insert -- The -- therefor.
Line 66, please delete "discharges" and insert -- discharged -- therefor.

Column 10,
Line 39, please delete "(As" and insert -- As -- therefor.
Line 43, please delete "715)." and insert -- 715. -- therefor.

UNITED STATES PATENT AND TRADEMARK OFFICE
CERTIFICATE OF CORRECTION

PATENT NO.    : 6,309,487 B1
DATED         : October 30, 2001
INVENTOR(S)   : Herrin et al.

It is certified that error appears in the above-identified patent and that said Letters Patent is hereby corrected as shown below:

Column 12,
Line 43, please delete "sea ling" and insert -- sealing -- therefor.

Signed and Sealed this

Sixth Day of August, 2002

Attest:

Attesting Officer

JAMES E. ROGAN
Director of the United States Patent and Trademark Office